US008060190B2

(12) United States Patent
Sörnmo et al.

(10) Patent No.: US 8,060,190 B2
(45) Date of Patent: Nov. 15, 2011

(54) DETECTION OF DRASTIC BLOOD PRESSURE CHANGES

(75) Inventors: Leif Sörnmo, Lund (SE); Kristian Solem, Lund (SE)

(73) Assignee: Gambro Lundia AB (SE)

( * ) Notice: Subject to any disclaimer, the term of this patent is extended or adjusted under 35 U.S.C. 154(b) by 671 days.

(21) Appl. No.: 11/662,480

(22) PCT Filed: Sep. 12, 2005

(86) PCT No.: PCT/SE2005/001326
§ 371 (c)(1),
(2), (4) Date: Nov. 13, 2008

(87) PCT Pub. No.: WO2006/031186
PCT Pub. Date: Mar. 23, 2006

(65) Prior Publication Data
US 2009/0082684 A1   Mar. 26, 2009

Related U.S. Application Data

(60) Provisional application No. 60/593,729, filed on Feb. 9, 2005.

(30) Foreign Application Priority Data

Sep. 13, 2004  (SE) ...................................... 0402184

(51) Int. Cl.
*A61B 5/0402* (2006.01)
(52) U.S. Cl. ........................................ 600/509; 600/485
(58) Field of Classification Search .................. None
See application file for complete search history.

(56) References Cited

U.S. PATENT DOCUMENTS 4,967,754 A   11/1990   Rossi
(Continued)

FOREIGN PATENT DOCUMENTS

JP          11-154       12/1999
JP       2003-190109     7/2003

OTHER PUBLICATIONS

Shapira, MD, et al., "ECG Changes and Cardiac Arrhythmias in Chronic Renal Failure Patients on Hemodialysis", Journal of Electrocardiology, vol. 25, No. 4, pp. 273-279, (Oct. 4, 1992).
Severi, et al., "Heart rate variability spectral indices for haemodynamic classification of haemodialysis patients", Physiol. Meas. 18, IOP electronic journals, pp. 339-353, (1997).
Birkett, et al., "Mechanisms Underlying Alterations in Power Spectra of Heart Rate Variability Associated with Ectopy", Computers in Cardiology, pp. 391-394, (1992).
(Continued)

*Primary Examiner* — Kennedy Schaetzle
(74) *Attorney, Agent, or Firm* — Finnegan, Henderson, Farabow, Garrett & Dunner LLP

(57) ABSTRACT

The invention relates to cardiac-activity based prediction of a rapid drop in a patient's blood pressure during hemodialysis. A proposed alarm apparatus includes an input interface, primary and secondary analysis units and an alarm-generating unit. An electrocardiogram signal ($H_{ECG}$) of the patient is received via the input interface by the primary analysis unit, which in response thereto produces a heart-rate-variability signal ($P_{HRV}$). The secondary analysis unit determines an intensity of ectopic beats ($P_{EBC}$) based on the electrocardiogram signal ($H_{ECG}$). The alarm-generating unit investigates whether the intensity of ectopic beats ($P_{EBC}$) is relatively low or relatively high. In case of a relatively low intensity, the unit triggers an alarm signal ($\alpha$) indicative of an estimated rapid blood pressure decrease if the heart-rate-variability signal ($P_{HRV}$) fulfills a first alarm criterion. In case of a relatively high intensity, however, the unit triggers the alarm signal ($\alpha$) if the intensity of the ectopic beats ($P_{EBC}$) fulfills a second alarm criterion.

30 Claims, 5 Drawing Sheets

U.S. PATENT DOCUMENTS

| | | | |
|---|---|---|---|
| 4,979,110 A * | 12/1990 | Albrecht et al. | 600/301 |
| 6,050,951 A * | 4/2000 | Friedman et al. | 600/485 |
| 6,736,789 B1 | 5/2004 | Spickermann | |
| 7,079,888 B2 | 7/2006 | Oung et al. | |
| 2003/0225162 A1 | 12/2003 | Schreiber et al. | |

OTHER PUBLICATIONS

Nissho KK, "Blood Dialyzer Equipped With Blood Pressure Monitoring Function", Patent Abstracts of Japan of JP 5285128 A, (Nov. 2, 1993).

* cited by examiner

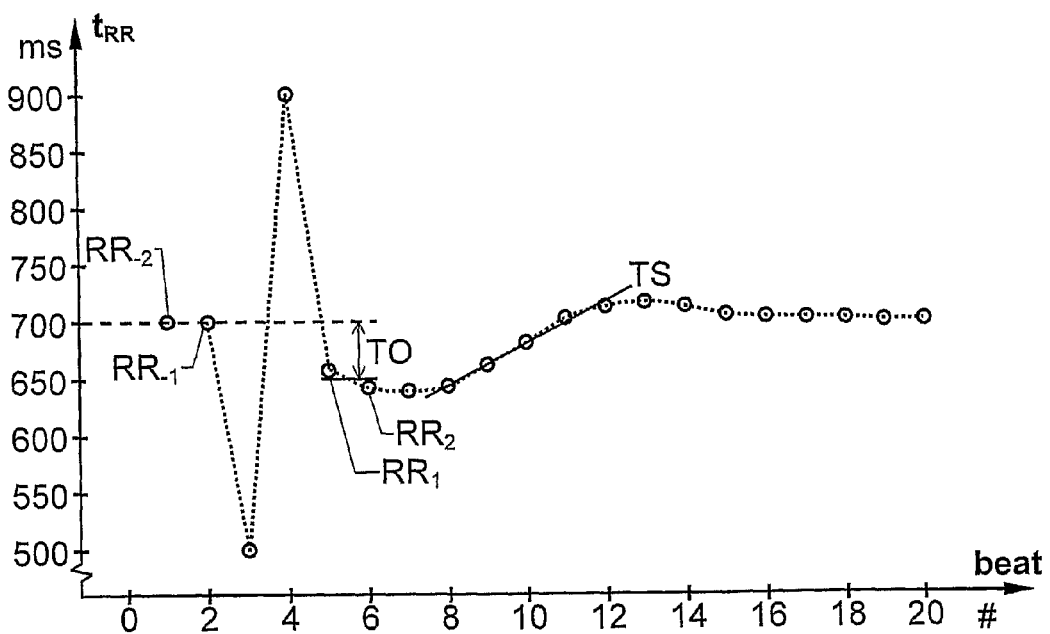
Fig. 10
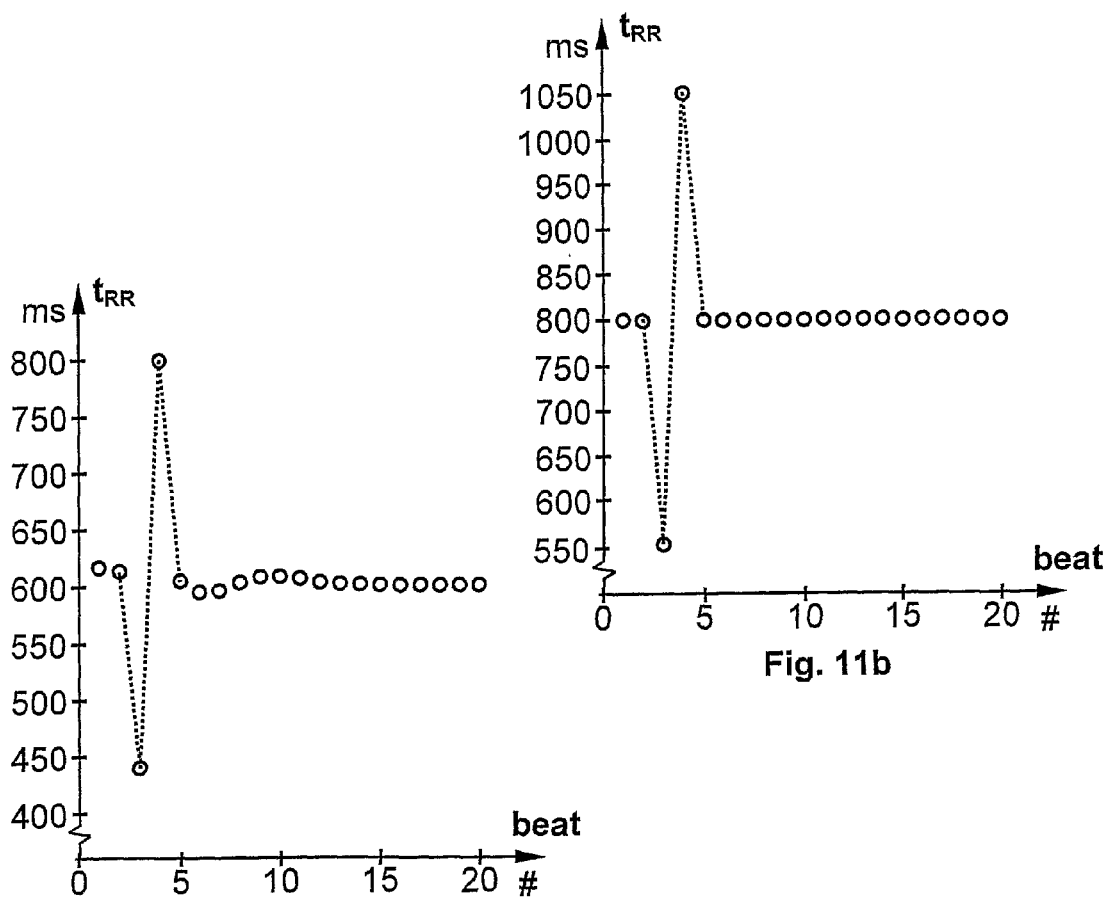
Fig. 11a
Fig. 11b

DETECTION OF DRASTIC BLOOD PRESSURE CHANGES

CROSS REFERENCE TO RELATED APPLICATIONS

This application is a national phase application based on PCT/SE2005/001326, filed Sep. 15, 2005, the content of which is incorporated herein by reference, and claims the priority of Swedish Patent Application No. 0402184-6, filed Sep. 13, 2004, and the benefit of U.S. Provisional Application No. 60/593,729, filed Feb. 9, 2005, the content of both of which is also incorporated herein by reference.

THE BACKGROUND OF THE INVENTION AND PRIOR ART

The present invention relates generally to detection of the onset of a rapid drop in a patient's blood pressure during hemodialysis. More particularly, the invention relates to an alarm apparatus for predicting a rapid blood pressure decrease in a patient undergoing hemodialysis treatment, a medical system comprising a dialysis apparatus configured to perform a hemodialysis treatment of a patient, a method for predicting a rapid blood pressure decrease in a patient undergoing hemodialysis treatment, a computer program relating to the above-identified method, and a computer readable medium also relating to the above-identified method.

The human body consists of approximately 60% water—a level which is important to maintain for survival. While it is unproblematic to provide the body with new water, disposal of surplus water is a major problem in renal patients. The task of the normal kidney is to remove superfluous fluid from the blood, such as water, urea and other waste products. The resulting urine is transferred to the bladder and finally leaves the body during urination. The kidney's second task is to regulate for example the balance of acid and base. With malfunctioning kidneys, disorders may develop in most major body organs, a syndrome called uremia. If uremia remains untreated, it will lead to death. Uremia is treated either by kidney transplantation or dialysis.

During dialysis, it is common that the patient suffers from symptomatic hypotension (i.e. a rapid blood pressure decrease), followed by nausea, vomiting and sometimes fainting. Such an event is not only strenuous for the patient, but also requires considerable attention from the staff overseeing the treatment. Consequently, during hemodialysis, it is highly desirable to detect the onset of symptomatic hypotension and preventing it from coming about.

In recent years, the connection between heart rate variability (HRV) and hypotension has been studied. HRV analysis has been proven to be a useful noninvasive tool for assessing information on the state of the autonomatic nervous system, and thus parasympathetic and sympathetic activity. If the HRV is analyzed in the frequency domain, the spectrum is often divided into two sub-bands: a low-frequency (LF) band, e.g. 0.04 Hz to 0.15 Hz, and a high-frequency (HF) band, e.g. 0.15 to 0.40 Hz. The effect on HRV due to changes in the autonomatic balance has been investigated in many studies, with the main conclusion that the LF band is influenced by sympathetic activity, whereas parasympathetic activity influences the HF band. Moreover, determinants of HRV in hemodialysis patients have been studied as well as autonomic dysfunction during hemodialysis.

In addition, the relationship between HRV and blood pressure during hemodialysis has been investigated. For instance, the patent document U.S. Pat. No. 4,718,891 describes an automated hemodialysis control based on this relationship. Although being silent about dialysis, the published International Patent Application WO99/59466 discloses a combined electrocardiogram (ECG) and blood-pressure measuring apparatus.

Today, little is known about sequential changes in the activity of the autonomatic nervous system, which occur just before and during a hypotensive episode. So far, the major attention has been focused on the relation between the power in the LF and the HF band, the so-called LF/HF ratio, in hypotension-prone and hypotension-resistant uremic patients. It has been concluded that the LF/HF ratio can be used as a hypotension marker in hemodialysis patients, since significant increase of the LF/HF ratio is observed during dialysis sessions not complicated by hypotension, whereas at the time of collapse, the LF/HF ratio fell markedly in sessions with hypotension. It has also been suggested that the LF/HF ratio may reveal differences between groups with different propensity to hypotension, and can thus give a deeper insight into the autonomatic control during dialysis. Hence, the LF/HF ratio appears to be a useful index for discriminating between hypotension-prone and hypotension-resistant patients. The sympathovagal balance has also been identified as a major determinant of short-term blood pressure variability. The sympathovagal balance describes the dual, opposing effects of the sympathetic and parasympathetic nervous systems on the sinus node.

In the article, "ECG Changes and Cardiac Arrhythmias in Chronic Renal Failure Patients on Hemodialysis", Journal of Electro-cardiology, Vol. 25, No. 4, October 1992, Shapira, O. M. et al. describe that patients with chronic renal failure frequently exhibit ECG changes and a high incidence of ventricular and supraventricular arrhythmias, which may be prognostically significant during and after hemodialysis. One very important effect of cardiac arrhythmias and other beat abnormalities, which may occur during dialysis, is that these events disturb the above-mentioned HRV analysis. As a result, the HRV-based techniques for predicting/detecting hypotension fail when ventricular ectopic beats (VEB) and supraventricular ectopic beats (SVEB) are too frequent. In such cases, the premature beats disrupt the neurocardiac modulation of the sinus rhythm and render adjacent RR intervals useless for HRV analysis.

However, there is yet no solution, which is capable of modeling the beat abnormality aspects of cardiac activity sufficiently well in order to detect, or predict, a rapid blood pressure change arising during an ongoing dialysis treatment.

SUMMARY OF THE INVENTION

The object of the present invention is therefore to alleviate the problems above and thus accomplish a solution by means of which the onset of a rapid blood pressure decrease can be detected at a point in time when any effects thereof, such as nausea and fainting, still can be avoided.

According to one aspect of the invention, the object is achieved by the initially described alarm apparatus, wherein the apparatus includes a secondary analysis unit and an alarm unit. The secondary analysis unit is adapted to determine an intensity of ectopic beats based on the electrocardiogram signal. The alarm-generating unit is adapted to investigate whether the intensity of ectopic beats is relatively low or relatively high. Provided that a relatively low intensity is determined, the alarm-generating unit triggers an alarm signal, indicative of an estimated rapid blood pressure decrease, if the heart-rate-variability signal fulfills a first alarm criterion. If however, the secondary analysis unit determines that the intensity of ectopic beats is relatively high, the alarm-generating unit triggers the alarm signal if the intensity of the ectopic beats fulfils a second alarm criterion.

An important advantage attained by this strategy is that the detrimental influence of ectopic beats may essentially be removed from the heart rate variability analysis. Thus, the first alarm criterion can be tested with a high degree of certainty. Furthermore, the onset of a rapid blood pressure decrease may be detected also when the intensity of ectopic beats is high. Hence, the two proposed techniques for detecting a blood pressure decrease complement one another very well, and here manage to characterize the two most important different aspects of cardiac activity.

According to a preferred embodiment of this aspect of the invention, the primary analysis unit includes a spectral analysis module, which is adapted to produce the heart-rate-variability signal as follows. First, a heart rate signal based on the electrocardiogram signal is transformed into a power spectrum representation of the electrocardiogram signal. Then, a ratio is calculated between an LF band and an HF band of said power spectrum representation. The first alarm criterion is considered to be fulfilled if the ratio is below a first threshold value.

In its capacity as a marker for blood pressure changes, this ratio is an advantageous test parameter for the heart rate variability. Namely, as mentioned initially, the LF band is influenced by the sympathetic activity, whereas the parasympathetic activity influences the HF band, and in hemodialysis sessions with hypotension it has been found that the HF power increases and the LF spectral power decreases. Consequently, the LF-to-HF ratio drops markedly in connection with a blood pressure decrease.

Preferably, the LF band ranges from approximately 0.04 Hz to approximately 0.15 Hz, the HF band ranges from approximately 0.15 Hz to approximately 0.40 Hz, and the first threshold value is approximately equal to one. Under typical conditions, the signal energy tends to be relatively evenly distributed between these two sub-bands. In connection with a blood pressure decrease however, the signal energy will be shifted up in frequency, such that a larger proportion of the signal energy is present above 0.15 Hz. Nevertheless, if an appropriate first threshold value is selected, any other band division is equally well conceivable according to the invention.

According to another preferred embodiment of this aspect of the invention, the apparatus includes a beat morphology analysis unit, which is adapted to: receive the electrocardiogram signal and pre-process this signal. The pre-processing involves classifying each segment of the electrocardiogram signal to represent a particular type of event. The beat morphology analysis unit produces a resulting enhanced electrocardiogram signal, which is equivalent to the original electrocardiogram signal, however where each signal segment is associated with relevant event-type data. Such a beat morphology analysis unit is desirable because it significantly facilitates a subsequent signal processing aiming at estimating the onset of a rapid blood pressure decrease.

Preferably, the event-type data includes: a normal beat (representing a beat whose morphology is typical for the patient), and an ectopic beat (representing a beat whose morphology is non-typical for the patient). However, in order to further improve the efficiency of the signal processing, the event-type data may also include an artifact type (representing a beat which neither fulfills the criteria for a normal nor for an ectopic beat), and a noise type (representing an undesired amount of energy contained in the electrocardiogram signal).

According to yet another preferred embodiment of this aspect of the invention, the primary analysis unit includes a rate detector module, which is adapted to receive the enhanced electrocardiogram signal, and based thereon produce the heart rate signal. Thereby, a reliable source signal for the spectral analysis is created.

According to still another preferred embodiment of this aspect of the invention, the secondary analysis unit is adapted to determine the intensity of ectopic beats based on the enhanced electrocardiogram signal. As mentioned above, this improves the signal processing.

According to a preferred embodiment of this aspect of the invention, the second alarm criterion is considered to be fulfilled if the intensity of ectopic beats exceeds a second threshold value. Preferably, the second threshold value represents a number equivalent to approximately four times a mean intensity of ectopic beats. Namely, by studying a mean parameter rather than an absolute ditto, a more reliable marker is attained. Moreover, a factor around four has been found to produce stable and reliable hypotension detection.

According to yet another preferred embodiment of this aspect of the invention, the apparatus comprises a third analysis unit, which is adapted to determine at least one heart-rate-turbulence parameter based on the electrocardiogram signal. Furthermore, the alarm generating unit is adapted to, in case of a relatively high intensity of ectopic beats, trigger the alarm signal if the at least one heart-rate-turbulence parameter fulfils at least one third alarm criterion. Thus, the chances are further improved that the onset of a rapid blood pressure decrease is detected at an early point in time.

According to still another preferred embodiment of this aspect of the invention, the at least one heart-rate-turbulence parameter includes a first parameter expressing a turbulence-onset measure reflecting a relative change in the RR-intervals of the electrocardiogram signal and/or a second parameter expressing a turbulence-slope measure reflecting a rise rate of the RR-intervals during a period following a particular ectopic beat. Namely, these parameters have been found to constitute reliable markers for the hypotension risk. Preferably, the at least one third alarm criterion is regarded as fulfilled if the first parameter exceeds a first turbulence threshold value. The at least one third alarm criterion is likewise regarded as fulfilled if the second parameter is outside a predefined interval delimited by a lower second turbulence value and an upper second turbulence value.

According to a further preferred embodiment of this aspect of the invention, the first parameter is determined as a difference between an average RR-interval shortly after a particular ectopic beat, say two RR-intervals, and an average RR-interval shortly before this ectopic beat, say two RR-intervals, divided by said average RR-interval shortly before the ectopic beat. Moreover, the first turbulence threshold value preferably represents a zero alteration of the RR-interval between shortly before to shortly after said ectopic beat. Hence, a reliable alarm criterion is defined.

According to yet another preferred embodiment of this aspect of the invention, the second parameter is determined based on a steepest slope found over a first set of RR-intervals, say five, within a second set of RR-intervals, say fifteen, following immediately after said ectopic beat in a function that expresses a time difference between consecutive R waves. Furthermore, the lower second turbulence value preferably represents one millisecond per RR-interval (i.e. a deceleration of 1 ms/RR-interval). Thus, another reliable alarm criterion is defined.

According to another aspect of the invention, the object is achieved by the initially described medical system, wherein the system further includes the proposed alarm apparatus, an electrocardiograph and a dialysis control unit. The electrocardiograph is adapted to register an electrocardiogram signal of the patient. The alarm apparatus receives the electrocardiogram signal, and the dialysis control unit is adapted to receive the proposed alarm signal from the alarm apparatus. In case of an alarm signal, the dialysis control unit transmits a control signal to the dialysis apparatus. The control signal, in turn, is adapted to cause an adjustment of at least one dialysis parameter in the dialysis apparatus (e.g. the ultrafiltration rate), such that an estimated risk that the patient enters a hypotension state is reduced. Of course, this system is desirable with respect to the patient's health and comfort, as well as with respect to staffing and other economical aspects.

According to a preferred embodiment of this aspect of the invention, the control signal is adapted to effect a complete interruption of the hemodialysis treatment performed by the dialysis apparatus. Thereby, the hypotension risk is further reduced.

According to another aspect of the invention the object is achieved by the initially described method, wherein an intensity of ectopic beats is determined based on the electrocardiogram signal. It is then investigated whether the intensity of ectopic beats for a current period is relatively high, or relatively low. During periods of relatively low ectopic beat intensity an alarm signal indicative of an estimated rapid blood pressure decrease is triggered if the heart-rate-variability signal fulfills a first alarm criterion. However, during periods of relatively high ectopic beat intensity the alarm signal is instead triggered if the intensity of ectopic beats fulfils a second alarm criterion.

The advantages of this method, as well as the preferred embodiments thereof, are apparent from the discussion hereinabove with reference to the proposed alarm apparatus.

According to a further aspect of the invention the object is achieved by a computer program directly loadable into the internal memory of a computer, comprising software for controlling the above proposed method when said program is run on a computer.

According to another aspect of the invention the object is achieved by a computer readable medium, having a program recorded thereon, where the program is to make a computer control the above proposed method.

Thus, by means of the invention, an essentially HRV-based analysis cannot only be prevented from failing in the presence of high ectopic beat intensity, but more important, a reliable prediction of a rapid blood pressure decrease can be achieved also under such conditions.

Further advantages, advantageous features and applications of the present invention will be apparent from the following description and the dependent claims.

BRIEF DESCRIPTION OF THE DRAWINGS

The present invention is now to be explained more closely by means of preferred embodiments, which are disclosed as examples, and with reference to the attached drawings.

DESCRIPTION OF PREFERRED
EMBODIMENTS OF THE INVENTION

Figure 1:
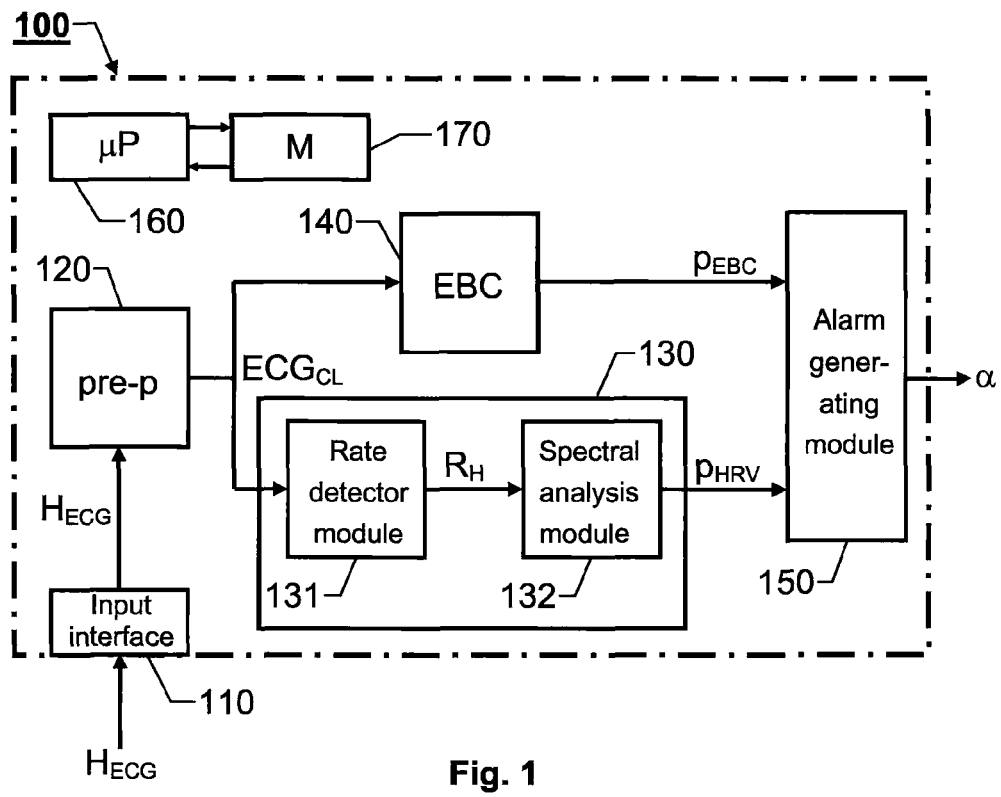
FIG. 1 shows a block diagram over an alarm apparatus according to a first embodiment of the invention.

FIG. 1 shows a block diagram over an alarm apparatus 100 for predicting a rapid blood pressure decrease in a patient undergoing dialysis treatment according to a first preferred embodiment of the invention.

The apparatus 100 includes an input interface 110, a primary analysis unit 130, a secondary analysis unit 140 and an alarm-generating unit 150. Preferably, the apparatus 100 also includes a central processing unit 160 for controlling the operation of the other units, and a memory medium 170 storing a computer program which in turn is adapted to control the central processing unit 160.

The input interface 110 is adapted to receive an electrocardiogram signal $H_{ECG}$ of the patient. For instance, the electrocardiogram signal $H_{ECG}$ is a bandpass filtered, digitized signal which has been sampled at a rate of 1000 Hz and has an amplitude resolution of 0.6 µV. The electrocardiogram signal $H_{ECG}$ is preferably registered by means of a reduced set of electrodes, e.g. an EASI lead system. However, naturally, utilization of other lead systems, e.g. the standard 12-lead system is likewise conceivable according to the invention.

The primary analysis unit 130 is adapted to produce a heart-rate-variability signal $p_{HRV}$ based on the electrocardiogram signal $H_{ECG}$. In order to accomplish this, the unit 130 preferably contains a rate detector module 131 and a spectral analysis module 132. The rate detector module 131 either receives the electrocardiogram signal $H_{ECG}$ per se, or receives an enhanced version thereof $ECG_{CL}$ produced by a beat morphology analysis unit 120, which may be included in the alarm apparatus 100 according to one preferred embodiment of the invention. Based on the electrocardiogram signal $H_{ECG}$ (or the enhanced electrocardiogram signal $ECG_{CL}$) the rate detector module 131 produces a heart rate signal $H_R$. The spectral analysis module 132 then receives heart rate signal $H_R$ and transforms it into a power spectrum representation of the electrocardiogram signal $H_{ECG}$ (i.e. a signal in the frequency domain). Based on the power spectrum, the module 132 calculates a ratio between a low-frequency (LF) band and a high-frequency (HF) band of the power spectrum. According to a preferred embodiment of the invention, the LF band ranges from approximately 0.04 Hertz to approximately 0.15 Hertz, and the HF band ranges from approximately 0.15 Hertz to approximately 0.40 Hertz. The operation of the primary analysis unit will be described in further detail below.

The secondary analysis unit 140 is adapted to determine an intensity of ectopic beats $p_{EBC}$ based on the electrocardiogram signal $H_{ECG}$ (or the enhanced electrocardiogram signal $ECG_{CL}$). Essentially, the intensity of ectopic beats $p_{EBC}$ is determined by applying signal processing which counts all cardiac beats that are outside the normal sinus rhythm. Also the operation principle of the secondary analysis unit 140 will be described in further detail below.

According to one preferred embodiment of the invention, the alarm apparatus 100 includes a beat morphology analysis unit 120. This unit is adapted to receive the electrocardiogram signal $H_{ECG}$, and pre-process it by classifying each segment of the signal $H_{ECG}$ to represent a particular type of event. The normal sinus rhythm is here classified as the dominant beat class of events, i.e. beats representing a morphology that is typical for the patient. An ectopic beat, however, represents a beat whose morphology is non-typical for the patient. Preferably, the beat morphology analysis unit 120 is also capable of identifying artifacts and noise, and allocating relevant event-type data. This means that beats which neither fulfill the criteria for a normal nor an ectopic beat are represented as artifacts, and the remaining undesired energy of the electrocardiogram signal $H_{ECG}$ is represented as noise.

Particularly, the beat morphology analysis unit 120 may be adapted to perform baseline filtering, QRS detection beat characterization and beat classification of the incoming electrocardiogram signal $H_{ECG}$. According one embodiment of the invention, the baseline filter is implemented as a linear-phase, finite impulse response lowpass filter which estimates a baseline wander followed by subtraction of this estimate from the original electrocardiogram signal $H_{ECG}$. Moreover, the baseline filter preferably complies with the American Heart Association (AHA) recommendations in terms of cut-off frequency for baseline filtering. After the baseline filtering, QRS detection is performed. Here, the beat occurrence times (i.e. the times of the R-waves) are detected. The fiducial point of each QRS complex is preferably defined by the peak location in an envelope signal obtained by summing the envelopes of each individual lead.

Following the QRS detection, each beat is classified as a normal or an ectopic beat (or an artifact or noise) based on a cross correlation method which i.a. makes use of the QRS morphology, beat-correlation and beat-SNR (signal-to-noise ratio). The cross-correlation method is initiated by using the first beat as a template beat. Each beat is subjected to linear-phase, bandpass filtering in order to remove frequencies which are deemed to be less essential for the classification. According to one preferred embodiment of the invention, the bandpass filter's cutoff frequencies are 1 and 35 Hz respectively.

Subsequently, each beat is compared to the set of template beats by computing the corresponding cross-correlation coefficients. Here, a coefficient is computed by shifting each beat in time until the best correlation is found. A new template beat is created whenever the cross-correlation drops below a noise-dependent threshold value. This type of threshold design is advantageous, since it ensures that the creation of new beat classes remains within reasonable limits in noisy signals. Preferably, the noise level is measured as a root-mean-square value of the highpass filtered samples contained in the RR-interval prior to a current QRS complex. According to a preferred embodiment of the invention, this highpass filtering is performed with a cutoff frequency at 20 Hz in order to avoid that P and T waves increase the noise level. A beat classified as being similar to an existing class is used to update the template beat by means of recursive averaging, thus gradually improving the quality of the template beats.

Consequently, the unit 120 generates an output signal in the form of an enhanced electrocardiogram signal $ECG_{CL}$, which is equivalent to the electrocardiogram signal $H_{ECG}$, however where each signal segment is at least associated with relevant event-type data.

The alarm-generating unit 150 investigates whether the intensity of ectopic beats $p_{EBC}$ is relatively low, or relatively high. In case of a relatively low intensity, the unit 150 triggers an alarm signal $\alpha$ indicative of an estimated rapid blood pressure decrease, if the heart-rate-variability signal $p_{HRV}$ fulfils a first alarm criterion. Given that the above-mentioned LF and HF sub-bands are selected, the first alarm criterion is considered to be fulfilled if the ratio is below a first threshold value, approximately equal to one.

In case of a relatively high intensity, the unit 150 triggers the alarm signal $\alpha$, if the intensity of the ectopic beats $p_{EBC}$ fulfils a second alarm criterion. According to one preferred embodiment of the invention, the second alarm criterion is fulfilled if the intensity of ectopic beats $p_{EBC}$ exceeds a second threshold value, which represents a number equivalent to approximately four times a mean intensity of ectopic beats.

Returning now to the HRV analysis performed by the primary analysis unit 130. This unit determines the heart rate variability based on the so-called heart timing (HT) representation, for instance by means of the integral pulse frequency modulation (IPFM) model. Said model may be used to simulate the variability of a series of occurrence times for normal sinus beats, and reflect the electrophysiological properties of the artria. The input signal to the IPFM model consists of the sum of a DC-level, related to the average heart rate, and a modulating signal m(t), related to the variability due to parasympathetic and sympathetic activity. The input signal to the IPFM model is integrated until a threshold, $\overline{T}_0$ (representing the mean interval length between successive events) is reached. Then, an event is created at time $t_k$ as output of the model, and the integrator is reset to zero. As a result, the output signal of the IPFM model becomes an event series, which represents the heart cycle occurrences in time. In mathematical terms, the following equation defines the series of event times:

$$\int_0^{t_k} (1 + m(\tau))d\tau = k\overline{T}_0 \quad K = 0, \ldots, N \tag{1}$$

where k is an integer that indexes the k:th beat following the initial beat, and the initial beat occurring at $t_0=0$. The function in (1) can be generalized to a continuous-time function by introducing the following definition:

$$\int_0^t (1 + m(\tau))d\tau = \kappa(t)\overline{T}_0 \tag{2}$$

The integral can now be calculated up to any time t and is proportional to an index function $\kappa(t)$ whose value at $t_k$ is identical to the integer beat index k, that is $\kappa(t_k)=k$.

The heart timing signal $d_{HT}(t)$ is defined at the event time $t_k$ as the difference between the event time $t_k$ and the expected occurrence time at the mean heart rate, $k\overline{T}_0$. The heart timing signal $d_{HT}(t)$ is closely related to the IPFM model and its modulating signal m(t). On the basis of the heart timing signal $d_{HT}(t)$, the modulating signal m(t) and especially its Fourier transform can be determined in order to produce an estimate of the HRV power spectrum.

The relationship between the heart timing signal $d_{HT}(t)$ and the modulating signal m(t) can be seen by studying the model equation (1) for a particular time $t_k$. The equation can be rewritten into:

$$\int_0^{t_k} m(\tau) d\tau = k\overline{T}_0 - t_k \equiv d_{HT}(t_k) \quad (3)$$

The mean RR interval length $\overline{T}_0$ must be estimated from the available data in order to compute $d_{HT}(t_k)$. This can be done by simply dividing the time $t_K$ of the last event with the number of events K, i.e.:

$$\overline{T}_0 = \frac{t_K}{K} \quad (4)$$

Using the generalized IPFM model in (2), the heart timing signal $d_{HT}(t)$ can be expressed in continuous-time as:

$$d_{HT}(t) = \int_{-\infty}^{t} m(\tau) d\tau \quad (5)$$

Since the modulating signal m(t) is assumed to be a causal function the integration interval can be extended to $-\infty$. If the Fourier transform of the modulating signal m(t) and the heart timing signal $d_{HT}(t)$ are denoted $D_m(\Omega)$ and $D_{HT}(\Omega)$ respectively, we have from (5) that:

$$D_{HT}(\Omega) = \int_{-\infty}^{\infty} d_{HT}(t) e^{-j\Omega t} dt = \frac{D_m(\Omega)}{j\Omega} \quad (6)$$

where $\Omega=2\pi F$ and $D_m(0)=0$, since m(t) was assumed to have a DC component equal to zero. Once the Fourier transform $D_{HT}(\Omega)$ of the heart timing signal $d_{HT}(t)$ is known a spectral estimate of the Fourier transform $D_m(\Omega)$ of the modulating signal m(t) can be computed. According to preferred embodiments of the invention, the spectral estimate $D_m(\Omega)$ is either obtained by a technique for unevenly sampled signals, or by interpolation and resampling followed use of the discrete Fourier transform (DFT).

As mentioned initially, ectopic beats introduce errors in the HRV analysis. Similar errors can also be introduced by missed beats or falsely detected beats, which may be the result of poor QRS detection. The errors are due to impulse-like artifacts in the RR intervals, introduced by the RR intervals adjacent to an ectopic beat. The impulse will introduce a noise component in the spectral analysis. This is why the RR intervals adjacent to an ectopic beat should not be used in the HRV analysis. The fact that ectopic beats occur in both patients and normal subjects shows that the importance of dealing with ectopic beats prior to spectra analyses of the heart rate signal.

In order to correct for an ectopic beat it is important to know whether a particular beat has a normal or ectopic origin. According to one preferred embodiment of the invention, the labeling is done with classification criteria mainly based on QRS morphology according to the above-mentioned cross-correlation method, however also based on rhythm. According to one preferred embodiment of the invention, this rhythm is determined by the rate detector module 131, and represented by the heart rate signal $R_H$. Based on QRS morphology it is then relatively straightforward to discriminate ventricular ectopic beats (VEB), since their morphologies differ substantially from a normal sinus beat. The same observation holds for false events caused by artifacts. Unfortunately, however, it is not especially easy to sort out supraventricular ectopic beats (SVEB), or similar ectopic beats, since these tend to have essentially the same morphologies as normal sinus beats. The SVEB:s usually differ only with respect to P wave morphology. Nevertheless, due to noise it is impossible to make a classification exclusively based on the P wave. Thus, in order to discriminate the SVEB:s one has to use an interval-based criterion, which is much less reliable.

As already mentioned, the beat class that reflects the normal sinus beat is classified as the dominant beat class. Hence, SVEB:s are often classified as dominant beats in the signal pre-processing performed by the beat morphology analysis unit 120. Only the SVEB:s that differ from the dominant QRS morphology are here classified as ectopic beats. In general, the majority of SVEB:s are therefore classified as ectopic beats based on an RR-criterion. The same holds for missing beats. An RR-interval which is prolonged (often twice the length of the mean RR-interval length) is classified as a missing beat. A missed beat introduces impulse-like artifacts in the RR-intervals similar to those of ectopic beats. Thus, RR-intervals in which a beat is missing must also be dealt with in the HRV analysis. Moreover, a missed beat debilitates the heart's pumping capacity in a similar way as the complete compensatory pause following a VEB.

Since ectopic beats interrupt the normal sinus modulated heart rhythm, only electrocardiogram signal $H_{ECG}$ segments containing occasional ectopic beats should be processed. In signal segments containing frequent ectopic beats the underlying sinus rhythm is too distorted to make any reliable conclusions. Therefore, according to the invention, such segments are excluded from the HRV analysis.

The spectral analysis module 132 handles ectopic beats in a very computationally efficient manner. Here, we assume that sinus beats occur at times $t_0, t_1, \ldots, t_K$, and that one ectopic beat occurs at time $t_e$ in the electrocardiogram signal $H_{ECG}$ (or $ECG_{CL}$). The time $t_e$ is not included in the series $t_0, t_1, \ldots, t_K$, and the sinus beat immediately preceding the ectopic beat occurs at $t_{ke}$ and the sinus beat immediately following the occurs at $t_{ke+1}$.

According to one preferred embodiment of the invention, the ectopic beats are dealt with by first concluding that an ectopic beat modifies the occurrence times of subsequent normal beats. By estimating this time shift, δ, the presence of ectopic beats can be accounted for by the following equation:

$$d_{HT}(t_k) = \begin{cases} k\overline{T}_0 - t_k & k = 0, \ldots, k_e \\ k\overline{T}_0 - t_k + \delta & k = k_e + 1, \ldots, K \end{cases} \quad (7)$$

In order to estimate the time shift δ we make use of (1), such that:

$$k_e \overline{T}_0 = \int_0^{t_{ke}} (1 + m(\tau)) d\tau \qquad (8)$$

and $$(k_e + 1)\overline{T}_0 = \int_{t_{ke}}^{t_{ke+1}-\delta} (1 + m(\tau)) d\tau \qquad (9)$$

Subtracting (8) from (9) gives us the equation:

$$\overline{T}_0 = \int_{t_{ke}}^{t_{ke+1}-\delta} (1 + m(\tau)) d\tau = t_{ke+1} - t_{ke} - \delta + \int_{t_{ke}}^{t_{ke+1}-\delta} m(\tau) d\tau \qquad (10)$$

We now introduce a new parameter, $\overline{m}_k$, according to:

$$\overline{m}_k = \begin{cases} \int_k^{k+1} m(\tau) d\tau & k \neq k_e \\ \int_{t_{ke}}^{t_{ke+1}-\delta} m(\tau) d\tau & k = k_e \end{cases} \qquad (11)$$

where $\overline{m}_k$ ($k \neq k_e$) is the integral of m(t) between the two normal heart beats at $t_k$ and $t_{k+1}$. This gives us:

$$\delta = t_{ke+1} - t_{ke} - \overline{T}_0 + \overline{m}_{ke} \qquad (12)$$

For the special case of a constant heart rate (a linear presumption on κ(t) or, in other words, m(t)=0 and $\overline{m}_{ke}$=0) we obtain an estimate $\hat{\delta}_0$ of the time shift δ according to:

$$\hat{\delta}_0 = t_{ke+1} - t_{ke} - \overline{T}_0 \qquad (13)$$

which is referred to as the zero order estimate of δ.

Further, we assume that the variations of the modulating signal m(t) are small within the integral interval, and thus the beat-to-beat variations in $\overline{m}_k$ are also small. Hence, a better estimate of $\overline{m}_{ke}$ is the value corresponding to the previous beat according to:

$$\hat{\overline{m}}_{ke,1} = \qquad (14)$$

$$\overline{m}_{ke-1} = \int_{t_{ke-1}}^{t_{ke}} m(\tau) d\tau = d_{HT}(t_{ke}) - d_{HT}(t_{ke-1}) = t_{ke-1} - t_{ke} + \overline{T}_0$$

This estimate, in combination with (12), gives us a first order estimate $\hat{\delta}_1$ of the time shift δ according to:

$$\hat{\delta}_1 = t_{ke+1} - 2t_{ke} + t_{ke-1} \qquad (15)$$

Note the similarity between (13) and (15), since (15) can be rewritten as:

$$\hat{\delta}_1 = t_{ke+1} - t_{ke} - (t_{ke} - t_{ke-1}) = \hat{\delta}_0 - \hat{d}_{ke-1,0} \qquad (16)$$

where $\hat{d}_{ke-1,0}$ is the zero order estimate of $d_{ke-1}$, with $d_k$ defined as:

$$d_k = t_{k+1} - t_k + \overline{T}_0 + \overline{m}_k = 0 \; k \neq k_e \qquad (17)$$

Note the close relationship between (12) and (17), since (17) becomes (12) when $k = k_e$.

One generalization of a higher order estimate of $\overline{m}_{ke}$ of the modulating signal m(t) is to include variations in $\overline{m}_k$. If we continue to update the estimate of $\overline{m}_k$ according to:

$$\overline{m}_{k,p} = \overline{m}_{k,p-1} + \Delta \overline{m}_{k-1,p} \qquad (18)$$

where $\Delta \overline{m}_{k-1,p}$ is the p:th order difference of $\overline{m}_{k-1}$ according to:

$$\Delta \overline{m}_{k-1,p} = \Delta \overline{m}_{k-1,p-1} - \Delta \overline{m}_{k-2,p-1} \qquad (19)$$

Then it can be proven that the N:th order estimate $\hat{\delta}_N$ of the time shift δ is given by the following recursion equation:

$$\hat{\delta}_N = \hat{\delta}_{N-1} - \hat{d}_{ke-1,N-1} \; N=1, 2, \ldots \qquad (20)$$

where $$\hat{\delta}_0 = t_{ke+1} - t_{ke} - \overline{T}_0 \qquad (21)$$

Instead of using the recursion in (20), we can express the N:th order estimate $\hat{\delta}_N$ of the time shift δ directly in terms of the occurrence times:

$$\hat{\delta}_N = \sum_{l=0}^{N+1} (-1)^l \binom{N+1}{l} t_{ke+1-l} \quad N = 1, 2, \ldots \qquad (22)$$

and N=0 is given by (21), however cannot be used, since it makes use of the mean RR interval length $\overline{T}_0$, which is yet unknown. Once an estimate of the time shift δ according to (22) is obtained, it is straightforward to update the estimate $\overline{T}_0$ of the mean RR interval length $\overline{T}_0$ according to:

$$\hat{\overline{T}}_0 = \frac{t_K - \hat{\delta}_N}{K}. \qquad (23)$$

Now $d_{HT}(t_k)$ in (7) can be calculated, since all the involved parameters are available.

Returning to the secondary analysis unit 140, this unit is adapted to perform an EBC analysis, where an intensity of ectopic beats $p_{EBC}$ is determined. The occurrence times $t_k$ of the ectopic beats may be described by a point process $p_e(t)$ according to:

$$p_e(t) = \sum_{k=1}^{N} \delta(t - t_k) \qquad (24)$$

where N is the number of ectopic beats present. The secondary analysis unit 140 studies the changes in the behavior of the occurrence times $t_k$ of the ectopic beats. A point process is characterized by its intensity. Thus, a change in the behavior of the occurrence times $t_k$ influences the intensity in the point process. Consequently, the EBC analysis follows the changes in the intensity of a point process.

A point process only gives present information about the ectopic beats and take no count of their history, i.e. the amount of ectopic beats. In order to include this information a count process, $N_e(t)$, is used according to one preferred embodiment of the invention. The count process describes the number of ectopic beats present up until the time t, i.e. the integral of the point process $p_e(t)$, defined as:

$$N_e(t) = k \; t_k \leq t < t_{k+1} \; k = 0, 1, \ldots, N \qquad (25)$$

Thus, the intensity of the point process $p_e(t)$ is connected to the slope of the count process.

The beats used in the EBC analysis are those classified as ectopic in the signal pre-processing by the beat morphology analysis unit 120. Consequently, the majority of the SVEB:s are not used in the EBC analysis, since the majority of these beats are classified as dominant in the signal pre-processing. As described above, missing beats and VEB:s have similar effects on the heart. Hence, the occurrence times of such events are also included in the EBC analysis.

The EBC analysis follows the changes in the intensity of ectopic beats $p_{EBC}$ throughout the entire signal. According to the invention, the EBC analysis can be performed both in real time and off-line. However, in order to have the alarm signal $\alpha$ control a dialysis apparatus, the EBC analysis must be executed in real time. An instantaneous intensity of the ectopic beats in the electrocardiogram signal $H_{ECG}$ cannot be obtained. Nevertheless, the mean intensity over a time block can be computed. This analysis is preferably performed in a sliding window over the enhanced electrocardiogram signal $ECG_{CL}$. Thus, the EBC analysis follows changes in the intensity of ectopic beats $p_{EBC}$ blockwise. According to the invention, the intensity of ectopic beats $p_{EBC}$ can be measured in many ways, two of which will be explicitly described below. A first method is based on a point process representation and a second method is based on a count process.

One assumption is that the occurrence times of the ectopic beats follow a Poisson process, since the Poisson process is a point process. Thus, the distances between the occurrence times are independent and exponential distributed with the intensity $\lambda$. If the same intensity $\lambda$ is assumed within a block, then the maximum likelihood estimate, $\hat{\lambda}$, of the intensity $\lambda$ is according to:

$$\hat{\lambda} = \frac{K}{\sum_{k=1}^{K} x[k]} \quad (26)$$

where $x[k]$ is the different distances between each occurrence time and K is the number of distances (i.e. one less than the number of ectopic beats). The result is intuitive, since the easiest way to measure the intensity of ectopic beats within a block is simply to count the number of ectopic beats within that block, which is basically the same as (26), since the denominator is essentially constant for large block sizes.

Alternatively, the occurrences of the ectopic beats may be described by means of the count process $N_e(t)$, and its corresponding discrete-time signal model $N_e[n]$. The count process $N_e(t)$ is a non decreasing function and may, within a block, be approximated with a straight line model according to:

$$N_e[n] = A + Bn \quad (27)$$

where B is the slope of the count process and thus an estimate of the intensity of ectopic beats.

The available data set includes the occurrence times of the ectopic beats, $\{t_k\}$ for $k=1, \ldots, N$. A data set $x''[k]$ describing the number of ectopic beats at time $t_k$ (in accordance to a count process), can be attained from $\{t_k\}$, where $x''[k]$ is an unevenly sampled signal. A new data set $x[k]$ is obtained when $x''[k]$ is interpolated and then evenly resampled. When assuming a linear model the least square error estimate $\hat{B}$ of the intensity B, for a given set of evenly sampled data, is:

$$\hat{B} = -\frac{6}{N(N+1)} \sum_{k=0}^{N-1} x[k] + \frac{12}{N(N^2-1)} \sum_{k=0}^{N-1} kx[k] \quad (28)$$

where $x[k]$ is the distances between each occurrence time and N is the number of ectopic beats.

Figure 2:
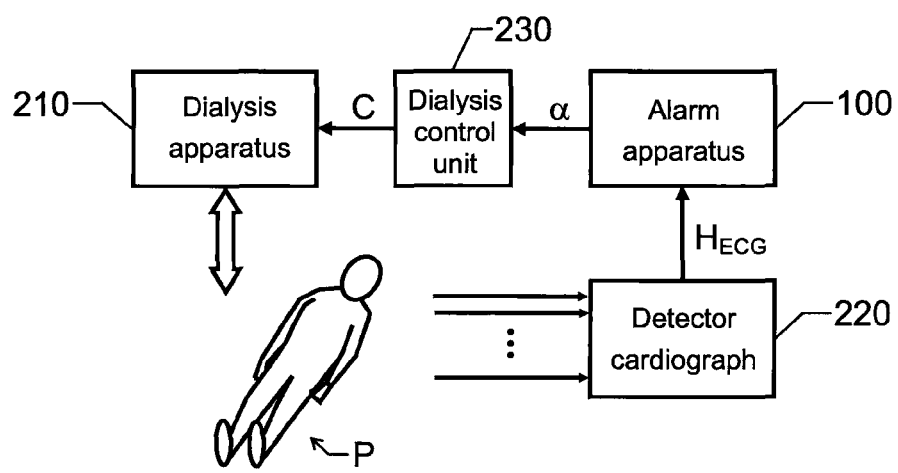
FIG. 2 shows an overview of a proposed medical system.

FIG. 2 shows an overview of a medical system according to one embodiment of the invention. The system includes a dialysis apparatus 210 for performing a hemodialysis treatment of a patient P. Additionally, an electrocardiograph 220, a dialysis control unit 230 and the proposed alarm apparatus 100 are included in the system. The electrocardiograph 220 registers an electrocardiogram signal $H_{ECG}$ of the patient P. For example, the electrocardiograph 220 may have a bandwidth of 0.05 Hz to 400 Hz, and the electrocardiogram signal $H_{ECG}$ may be a digitized signal which is sampled at a rate of 1000 Hz and has an amplitude resolution of 0.6 μV. Moreover, the electrocardiogram signal $H_{ECG}$ is preferably registered by means of a reduced set of electrodes, e.g. an EASI 5-lead system. The alarm apparatus 100 receives the electrocardiogram signal $H_{ECG}$. If either of the first or second alarm criteria is found to be fulfilled, the apparatus 100 produces an alarm signal $\alpha$ indicative of an estimated rapid blood pressure decrease. The dialysis control unit 230 receives this signal $\alpha$, and based thereon generates a control signal C to the dialysis apparatus 210. The control signal C, in turn, causes the dialysis apparatus 210 to adjust at least one dialysis parameter, e.g. the ultrafiltration rate, so that the estimated risk that the patient P enters a hypotension state is reduced.

According to one preferred embodiment of the invention, the control signal C effects a complete interruption of the dialysis treatment performed by the hemodialysis apparatus 210.

Of course, the dialysis control unit 230 need not be a separate unit (as illustrated in FIG. 2). Instead, this unit may be included in either one of the alarm apparatus 100, or the dialysis apparatus 210.

Figure 3:
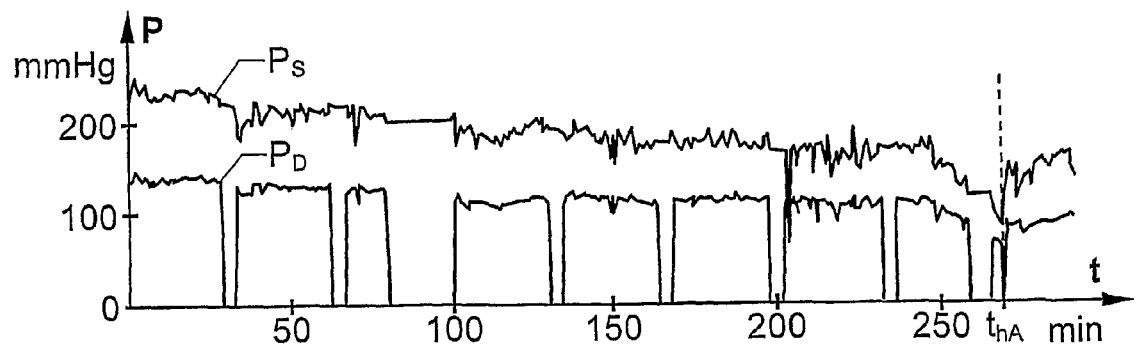
FIG. 3 shows a graph illustrating a first example of a patient's blood pressure variation during hemodialysis.

FIG. 3 shows a graph, which illustrates how a patient's arterial blood pressure (sampled at 200 Hz) varied during a hemodialysis treatment when the invention was not applied. However, it is estimated that the above-proposed strategies would have been capable of predicting the blood pressure decrease at a point in time prior to $t_{hA}$ when the hypotension still could have be avoided had the appropriate measures been taken after generation of the alarm signal $\alpha$.

The vertical axes show systolic pressures $P_S$ and diastolic pressures $P_D$, and the horizontal axes show the time t. In the example shown in FIG. 3 the patient suffered from acute symptomatic hypotension at a time $t_{hA}=268$ minutes after initiating the treatment. As can be seen in the graph, both pressures $P_S$ and $P_D$ drop rapidly before hypotension occurs.

Figure 4A:
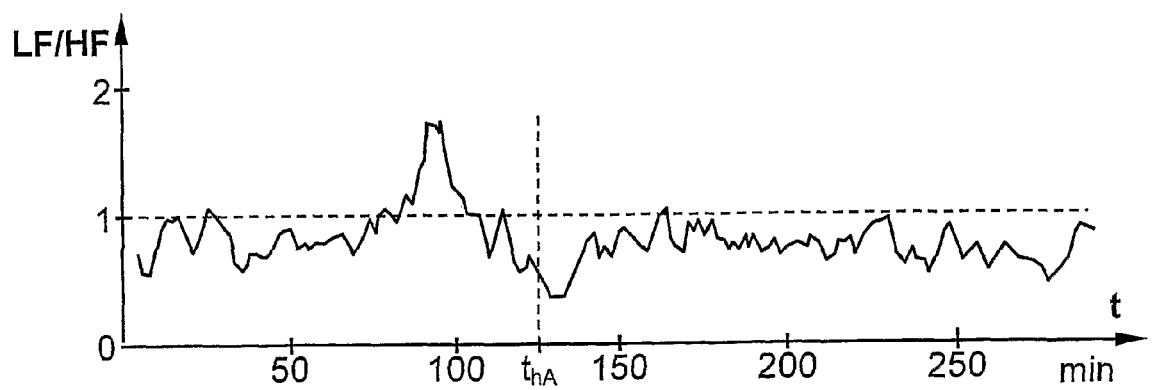
FIG. 4a shows a graph which illustrates how the ratio between an LF band and an HF band of a third patient's ECG power spectrum varies during a hemodialysis treatment.

FIG. 4a shows a graph which illustrates how a third patient's ratio LF/HF between a low-frequency (LF) band and a high-frequency (HF) band of an ECG power spectrum varies during a hemodialysis treatment. The HRV analysis was here performed according to the invention, i.e. all ectopic beats were handled before calculating the ratio LF/HF.

The vertical axis shows the ratio LF/HF and the horizontal axis represents the time t. A threshold value of LF/HF=1, indicated by means of a dashed line, illustrates the proposed first alarm criterion. As can be seen, in this example the ratio LF/HF is too low (i.e. below the threshold value 1) almost during the entire treatment. The patient made a slight head-up tilt around t≈100 minutes, which resulted in an increased ratio LF/HF exceeding the threshold value. Then, at t=$t_{hA}$ (≈125 minutes), the ratio LF/HF dropped sharply and acute symptomatic hypotension occurred.

Figure 4B:
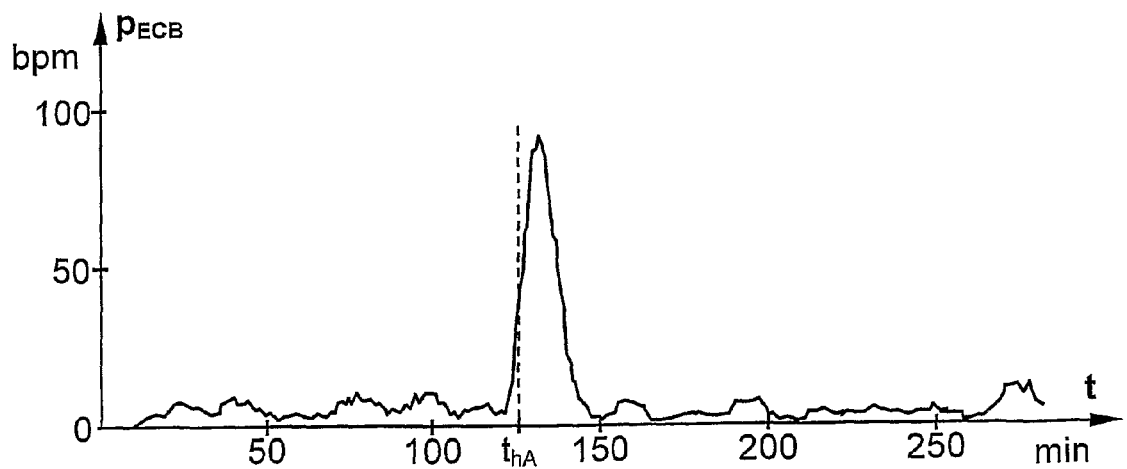
FIG. 4b shows a graph, corresponding to FIG. 4a, which demonstrates how the intensity of ectopic beats is developed for the third patient.

FIG. 4b shows a graph, corresponding to FIG. 4a, which demonstrates how the intensity of ectopic beats $p_{ECB}$ developed for the third patient. As is apparent from the graph, the intensity $p_{ECB}$ increased rapidly before t=$t_{hA}$. Thus, the proposed second alarm criterion would have been fulfilled before t=$t_{hA}$, and the hypotension could have been prevented.

Figure 5:
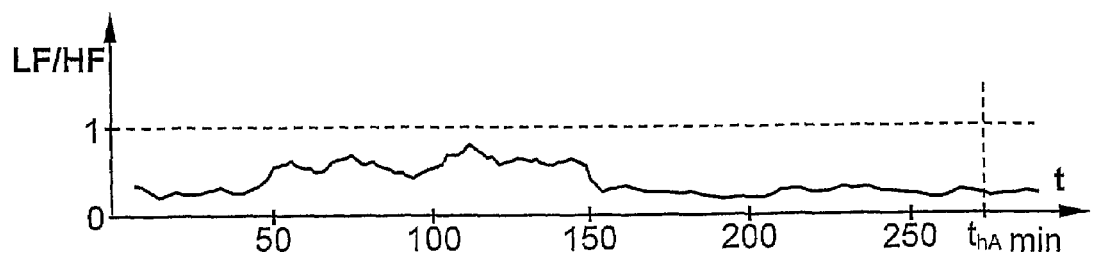
FIG. 5 shows a graph which illustrates how the ratio between an LF band and an HF band of a hypotension-prone patient's ECG power spectrum varies during a hemodialysis treatment.

FIG. 5 shows a graph which illustrates, by means of an example, how a ratio LF/HF between the LF band and the HF band of the ECG power spectrum may vary during a hemodialysis treatment for a patent who is relatively hypotension-prone. Here, there are no dramatic changes in the ratio LF/HF; only a minor increase between t=100 minutes to t=150 minutes due to eating. However, the ratio LF/HF never exceeds the threshold value 1, which indicates a high hypotension risk. Consequently, in this case, symptomatic hypotension occurred at t=$t_{hA}$ (≈270 minutes).

Figure 6:
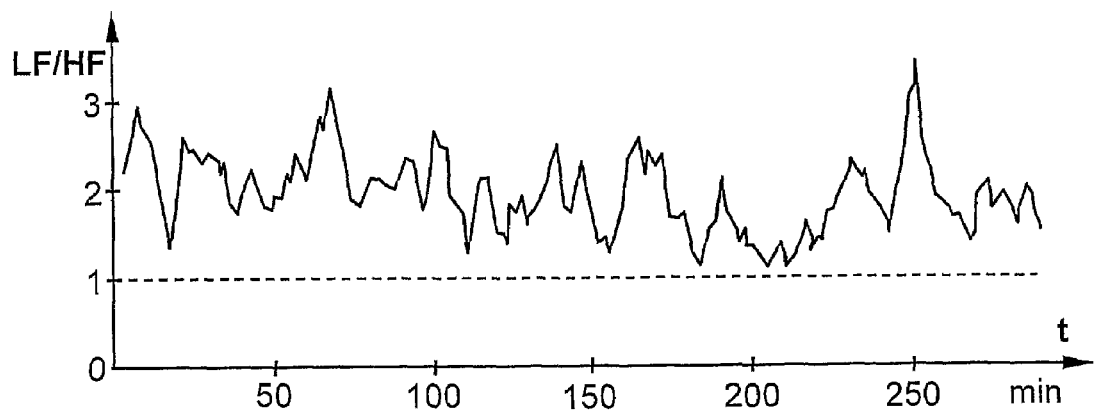
FIG. 6 shows a graph which illustrates how the ratio between an LF band and an HF band of a hypotension-resistant patient's ECG power spectrum varies during a hemodialysis treatment.

FIG. 6 shows a graph which illustrates, by means of an example, how the ratio LF/HF may vary during a hemodialysis treatment for a patent who is relatively hypotension-resistant. Again, the threshold value at LF/HF=1 is indicated by means of a dashed line. As opposed to the example shown in FIG. 6, the ratio LF/HF is here very high (permanently above 1, thus indicating a low hypotension risk), and although the ratio LF/HF varied substantially no hypotension occurred. This can be explained the patient being relatively hypotension-resistant and having a stable blood pressure.

Figure 7:
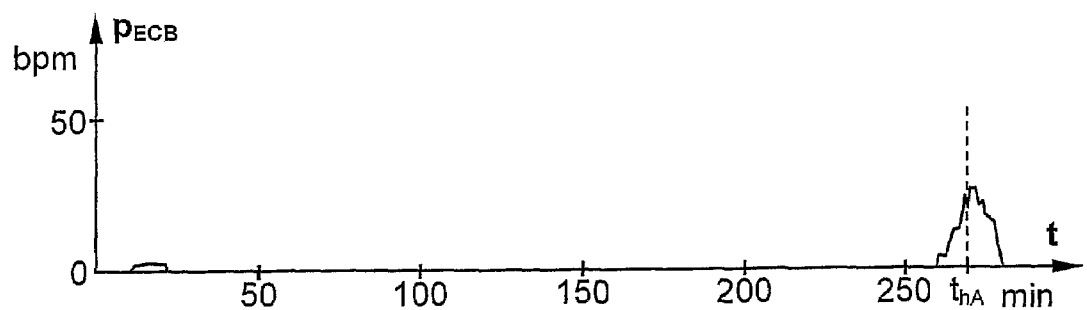
FIG. 7 shows a graph, which illustrates how the intensity of ectopic beats may be used as a basis for triggering an alarm signal.

FIG. 7 shows a graph, which illustrates how the intensity of ectopic beats $p_{ECB}$ developed for the above-mentioned first patient (see FIG. 3). In this case, practically no ectopic beats at all were registered until around t=260 minutes when the intensity of ectopic beats $p_{ECB}$ increased dramatically. Shortly there after, at $t_{hA}$=268 minutes, the patient suffered from acute symptomatic hypotension. An appropriately selected second alarm criterion according to the invention would certainly have predicted this.

Figure 8:
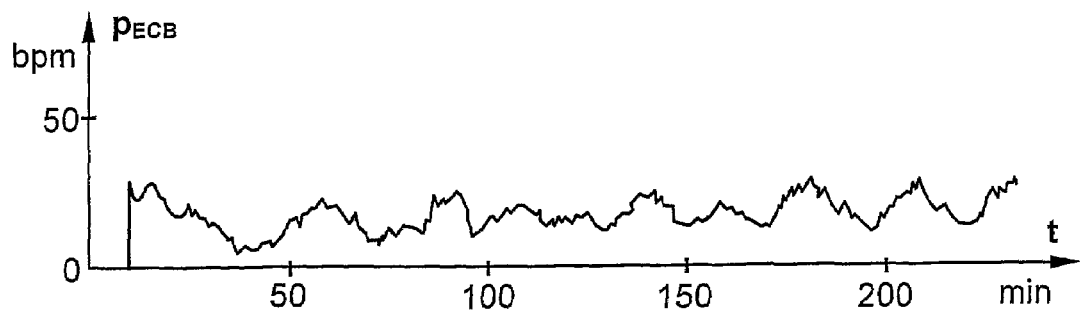
FIG. 8 shows a graph, which demonstrates that preferably a relative threshold value be used for triggering the alarm signal based on the intensity of ectopic beats.

FIG. 8 shows a graph over a patient's intensity of ectopic beats $p_{ECB}$ that is comparatively high throughout an entire dialysis treatment of the patient. However, here hypotension never occurred. This can be explained by the fact that the patient in this case is relatively hypotension-resistant. It should also be noted that the intensity of ectopic beats $p_{ECB}$ here never deviates exceedingly from a mean value (around approximately 30 bpm). Therefore, an appropriately selected second alarm criterion equivalent to roughly four times the mean intensity of ectopic beats, say at 120 bpm, would not have been fulfilled.

Figure 9:
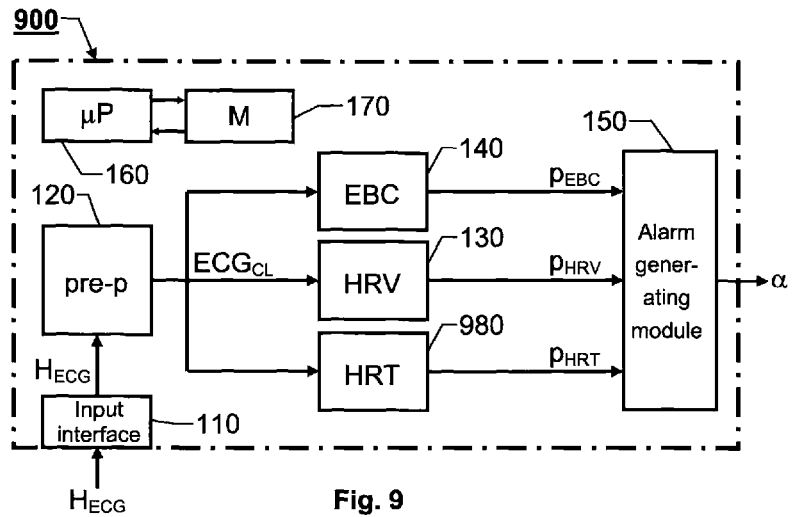
FIG. 9 shows a block diagram over an alarm apparatus according to a second embodiment of the invention, FIG. 10 demonstrates two proposed heart-rate-turbulence related parameters in a graph illustrating how the RR-intervals may vary in connection with an ectopic beat, FIGS. 11a, b show graphs which illustrate typical variations in the RR-intervals in connection with an ectopic beat for a hypotension-resistant and a hypotension-prone patient respectively.

FIG. 9 shows a block diagram over an alarm apparatus 900 according to a second embodiment of the invention. All elements, units and signals associated with reference symbols also occurring in the FIG. 1 designate the same elements, units and signals as those described above with reference to this figure.

Nevertheless, in addition to the units of the first embodiment of the invention shown in the FIG. 1, the apparatus 900 includes a third analysis unit 980. This unit is adapted to determine at least one heart-rate-turbulence (HRT) parameter $p_{HRT}$ based on the electrocardiogram signal $H_{ECG}$, or the enhanced version thereof $ECG_{CL}$. Naturally, in this embodiment, the alarm generating unit 150 is also adapted to trigger the alarm signal α if the at least one HRT parameter $p_{HRT}$ fulfils at least one third alarm criterion. Specifically, the at least one HRT parameter $p_{HRT}$ is primarily tested if the intensity of ectopic beats $p_{EBC}$ is relatively high (i.e. a determination being based upon the signal produced by the secondary analysis unit 140).

The rationale behind the test of the at least one HRT parameter $p_{HRT}$ is that, for normal subjects (i.e. being relatively hypotension resistant), the heart rate should increase immediately after a VEB, and then during a subsequent period return to baseline again. These short-term fluctuations in the heart rate are referred to as heart rate turbulence. It is believed that the heart rate is increased in order to compensate for a sudden local blood pressure drop induced by the VEB. Once the blood pressure level is restored, the heart rate returns to baseline again in order to stabilize the blood pressure. Consequently, HRT is desirable, and the degree of turbulence may be regarded as a subject's ability to recover from a local blood pressure drop, thereby avoiding hypotension.

We will now illustrate how the degree of turbulence can be measured with reference to FIG. 10. Here, a graph is shown, which illustrates how the RR-intervals may vary in connection with an ectopic beat for a patient. The horizontal axis shows the heart beat numbers #, and the vertical axis reflects the time between two consecutive R waves in the electrocardiogram, i.e. the RR-intervals $t_{RR}$.

The baseline is illustrated by means of a dashed line at an RR-interval around 700 ms. In this example, a first and a second beat are normal beats. However, for a third ectopic beat the RR-interval falls to approximately 500 ms, and for a fourth beat (i.e. between the ectopic beat and next normal beat) the RR-interval is prolonged to approximately 900 ms. Hence, these variations in the RR-intervals are induced by a VEB.

A first proposed HRT parameter $p_{HRT}$ expresses a turbulence-onset measure TO reflecting a relative change in the RR-intervals of the electrocardiogram signal $H_{ECG}$. TO is a measurement of the initial acceleration in the heart rate after the VEB. According to one preferred embodiment of the invention, the turbulence-onset measure TO is determined as a difference between an average RR-interval shortly before a particular VEB and an average RR-interval shortly after this beat divided by the average RR-interval shortly after said beat. This may be expressed as:

$$TO = 100 \cdot \frac{(RR_1 + RR_2) - (RR_{-2} + RR_{-1})}{(RR_{-2} + RR_{-1})} \quad [\%]$$

where $RR_{-1}$ denotes the RR-interval immediately before the VEB, $RR_{-2}$ denotes the RR-interval before $RR_{-1}$, $RR_1$ denotes the RR-interval immediately after the VEB, and $RR_2$ denotes the RR-interval after $RR_1$.

In the example shown in the FIG. 10, TO≈−7%, which is a healthy value. Essentially, any value below 0% can be regarded as healthy. Therefore, according to one preferred embodiment of the invention, the alarm generating unit 150 applies a first turbulence threshold value representing a zero alteration of the RR-interval between shortly before to shortly after a VEB, such that the alarm signal α is trigged if TO>zero.

A second parameter TS expresses a turbulence-slope measure reflecting how quickly the RR-intervals rise after a VEB, i.e. the declaration of the heart rate back to baseline again.

According to one preferred embodiment of the invention, the second parameter TS is determined based on a steepest (positive) slope of the RR-interval graph found over a first set of RR-intervals within a second set of RR-intervals following immediately after the VEB.

Healthy subjects generally have a heart rate declaration of at least 1 ms/RR-interval after the initial rate increase. Therefore, according to one preferred embodiment of the invention, after each VEB, a steepest positive slope over five RR-intervals (i.e. the above-mentioned first set) is determined within 15 RR-intervals (i.e. the second set above) following immediately after the VEB. Then the alarm generating unit 150 compares this steepest slope with a second turbulence threshold value representing one millisecond per RR-interval. If the second parameter TS is lower than this value, the alarm generating unit 150 triggers the alarm signal α. However, also an exceedingly high TS value may indicate an unhealthy condition. Therefore, in the general case, the alarm generating unit 150 preferably triggers the alarm signal a if the second parameter TS falls outside a predefined interval delimited by a lower second threshold value and an up per second threshold value.

Naturally, according to the invention, the first and second sets may comprise any number of RR-intervals other than five and fifteen provided that second set>first set.

FIG. 11a shows a graph, which again illustrates how the RR-intervals may vary in connection with a VEB for a hypotension-resistant patient. The baseline here lies an RR-interval around 600 ms. Then, comes a third beat, which is ectopic, wherein the RR-interval first decreases to 445 ms. The RR-interval to a following normal beat is prolonged to 800 ms. Subsequently, a short acceleration of the heart rate follows, and finally, the rate decelerates down to an RR-interval of 600 ms again.

FIG. 11b shows a graph illustrating an example of the variations in the RR-intervals in connection with VEB for a hypotension-prone patient. In this case, the subject has an RR-interval baseline at approximately 800 ms. This rate is temporarily altered around a third and a fourth heart beat, where the RR-intervals are 550 ms and 1050 ms respectively, due to the VEB. However, already at a fifth heartbeat the rate is back at the baseline 800 ms again. In other words, the steepest slope measured by the second parameter TS is inadequate, and due to the lack of compensation for the sudden blood pressure decrease after the VEB, the subject may experience nausea, and risks to faint. Of course, this risk is further increased if more VEB:s follow shortly, i.e. if the intensity of ectopic beats is relatively high. This parameter, in turn, is reflected by the signal $p_{EBC}$ generated by the secondary analysis unit 140. According to one preferred embodiment of the invention, the at least one-HRT parameter $p_{HRT}$ is tested primarily when the signal $p_{EBC}$ indicates a relatively high intensity of ectopic beats.

Figure 12:
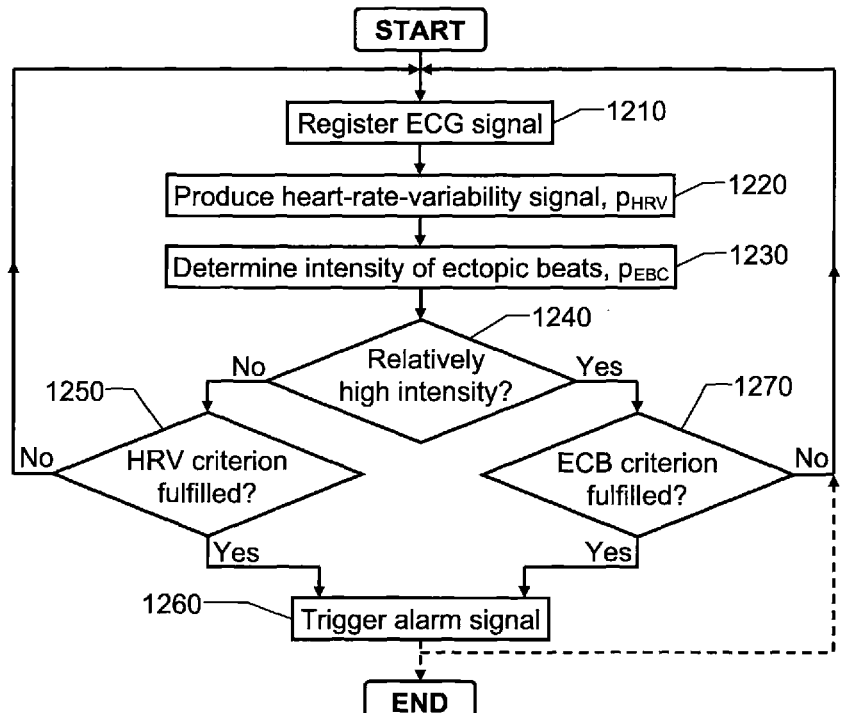
FIG. 12 shows a flow diagram which illustrates the general method according to the invention.

In order to sum up, the general method according to the invention will be described below with reference to the flow diagram in FIG. 12.

A first step 1210 registers an electrocardiogram signal of a patient. Then, a step 1220 produces a heart rate variability signal based on the electrocardiogram signal. Based on the electrocardiogram signal, an intensity of ectopic beats is subsequently determined in a step 1230. After that, a step 1240 investigates whether the intensity of ectopic beats for a current period is relatively high. If the step 1240 finds that the intensity ectopic beat intensity is not relatively high (i.e. the intensity is relatively low), a step 1250 follows. Otherwise, a step 1270 follows.

The step 1250 checks whether the heart-rate-variability signal fulfills a first alarm criterion (i.e. with respect to the HRV), and if so the procedure continues to a step 1260. The step 1270 checks whether the intensity of ectopic beats fulfills a second alarm criterion (i.e. with respect to ECB), and if so the procedure also continues to the step 1260. The step 1260 triggers an alarm signal indicative of an estimated rapid blood pressure decrease.

If neither the first alarm criterion of the step 1250, nor the second alarm criterion of the step 1270 is found to be fulfilled, the procedure loops back to the step 1210. The procedure may also return to the step 1210 after the step 1260. However alternatively, the procedure may end after 1260. Particularly, the latter may be the case if the hemodialysis treatment is interrupted in case of an alarm.

It is worth noting that the sequential procedure described above is only relevant for a particular segment of the electrocardiogram signal. Thus, in an implementation, e.g. a second signal segment is received according the step 1210 while the heart-rate-variability signal is produced for a first signal segment according to the step 1220, and so on.

Furthermore, all of the process steps, as well as any subsequence of steps, described with reference to the FIG. 12 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The carrier may be any entity or device capable of carrying the program. For example, the carrier may comprise a storage medium, such as a Flash memory, a ROM (Read Only Memory), for example a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

It should be noted that in this specification the term "predict" is given a very broad meaning, so that the point in time when a fulfilled alarm criterion is established and the point in time when said blood pressure decrease actually occurs may essentially coincide. Consequently, the alarm signal in this case represents a detection of the rapid blood pressure decrease rather than a prediction thereof.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. An alarm apparatus for predicting a rapid blood pressure decrease in a patient undergoing hemodialysis treatment, comprising:
    an input interface adapted to receive an electrocardiogram signal ($H_{ECG}$) of the patient;
    a primary analysis unit adapted to produce a heart-rate-variability signal ($p_{HRV}$) based on the electrocardiogram signal ($H_{ECG}$);
    a secondary analysis unit adapted to determine an intensity of ectopic beats ($p_{EBC}$) based on the electrocardiogram signal ($H_{ECG}$);
    an alarm generating unit adapted to investigate whether the intensity of ectopic beats ($p_{EBC}$) is relatively low or relatively high, said alarm generating unit being configured to trigger an alarm signal ($\forall$) indicative of an estimated rapid blood pressure decrease if the heart-rate-variability signal ($p_{HRV}$) fulfills a first alarm criterion, when said intensity of ectopic beats is relatively low, and said alarm generating unit being further configured to trigger said alarm signal ($\forall$) indicative of an estimated rapid blood pressure increase if the heartrate variability signal ($P_{HRV}$) fulfills a second alarm criterion, when said intensity of ectopic beats is relatively high.

2. The alarm apparatus according to claim 1, wherein the primary analysis unit comprises a spectral analysis module adapted to produce the heart-rate-variability signal ($P_{HRV}$) by:
    transforming a heart rate signal ($H_R$) based on the electrocardiogram signal ($H_{ECG}$) into a power spectrum representation of the electrocardiogram signal ($H_{ECG}$); and
    calculating a ratio ($p_{HRV}$) between a low-frequency band and a high-frequency band of said power spectrum representation, wherein said first alarm criterion is fulfilled if the ratio ($P_{HRV}$) is below a first threshold value.

3. The alarm apparatus according to claim 2, wherein the low-frequency band ranges from approximately 0.04 Hertz to approximately 0.15 Hertz, the high-frequency band ranges from approximately 0.15 Hertz to approximately 0.04 Hertz, and the first threshold value is approximately equal to one.

4. The alarm apparatus according to claim 1, wherein the alarm apparatus comprises a beat morphology analysis unit adapted to:
    receive the electrocardiogram signal ($H_{ECG}$), said electrocardiagram signal having multiple segments;
    pre-process the electrocardiogram signal ($H_{ECG}$), the pre-processing involving classifying each segment of the electrocardiogram signal ($H_{ECG}$) to represent a particular type of event; and
    producing an enhanced electrocardiogram signal ($ECG_{CL}$) equivalent to the electrocardiogram signal ($H_{ECG}$) wherein each signal segment is associated with relevant event-type data.

5. The alarm apparatus according to claim 4, wherein said event-type data comprises:
    a normal beat representing a beat having a morphology typical for a patient; and
    an ectopic beat representing a beat having a morphology non-typical for the patient.

6. The alarm apparatus according to claim 5, wherein said event-type data further comprises at least one of:
    an artifact representing a beat that neither fulfills the criteria for a normal beat nor an ectopic beat; and
    noise representing undesired energy of the electrocardiogram signal ($H_{ECG}$).

7. The alarm apparatus according to claim 4 or 5, wherein the primary analysis unit comprises a rate detector module adapted to receive the enhanced electrocardiogram signal ($ECG_{CL}$), and configured to produce a heart rate signal ($H_R$) based on said enhanced electrocardiogram signal ($ECG_{CL}$).

8. The alarm apparatus according to one of claim 4 5, or 6, wherein the secondary analysis unit is configured to determine the intensity of ectopic beats ($P_{EBC}$) based on the enhanced electrocardiogram signal ($ECG_{CL}$).

9. The alarm apparatus according to claim 1, wherein the second alarm criterion is fulfilled if the intensity of ectopic beats ($P_{EBC}$) exceeds a second threshold value.

10. The alarm apparatus according to claim 9, wherein the second threshold value represents a number equivalent to approximately four times a mean intensity of ectopic beats.

11. The alarm apparatus according to claim 1, wherein the apparatus comprises a third analysis unit configured to determine at least one heart-rate-turbulence parameter ($p_{HRT}$) based on the electrocardiogram signal ($H_{ECG}$); and the alarm generating unit is further configured, in case of a relatively high intensity of ectopic beats ($p_{EBC}$), to trigger the alarm signal ($\forall$) if the at least one heart-rate-turbulence parameter ($P_{HRT}$) fulfils at least one third alarm criterion.

12. The alarm apparatus according to claim 11, wherein the at least one heart-rate-turbulence parameter ($p_{HRT}$) comprises at least one of:
    a first parameter (TO) expressing a turbulence-onset measure reflecting a relative change in the RR-intervals of the electrocardiogram signal ($H_{ECG}$); and
    a second parameter (TS) expressing a turbulence-slope measure reflecting a rise rate of the RR-intervals during a period following a particular ectopic beat.

13. The alarm apparatus according to claim 12, wherein one third alarm criterion is fulfilled if:
    the first parameter (TO) exceeds a first turbulence threshold value; or
    the second parameter (TS) is outside an interval delimited by a lower second turbulence value and an upper second turbulence value.

14. The alarm apparatus according to claim 13, wherein the first parameter (TO) is determined as a difference between an average RR-interval shortly after ($RR_1$, $RR_2$) a particular ventricular ectopic beat and an average RR-interval shortly before ($RR_{-2}$, $RR_{-1}$) the particular ventricular ectopic beat divided by the average RR-interval shortly before ($RR_{-2}$, $RR_{-1}$) said particular ventricular ectopic beat, said first turbulence threshold value representing a zero alteration of the RR-interval from shortly before to shortly after said ventricular ectopic beat.

15. The alarm apparatus according to claim 13 or 14, wherein the second parameter (TS) is determined based on a steepest slope found over a first set of RR-intervals within a second set of RR-intervals following immediately after said ventricular ectopic beat in a function expressing a time difference between consecutive R waves in the electrocardiogram signal ($H_{ECG}$); and said lower second turbulence value represents one millisecond per RR-interval.

16. A medical system comprising a dialysis apparatus adapted to perform a hemodialysis treatment of a patient, wherein the system further comprises:
    an electrocardiograph configured to register an electrocardiogram signal ($H_{ECG}$) of the patient;
    an alarm apparatus according to claim 1 receiving said electrocardiogram signal ($H^{ECG}$); and
    a dialysis control unit configured to receive the alarm ($\forall$) signal from the alarm apparatus, and based on the alarm signal ($\forall$), transmit a control signal to the dialysis apparatus, said control signal being configured to cause an adjustment of at least one dialysis parameter in the dialysis apparatus such that an estimated risk that the patient enters a hypotension state is reduced.

17. The medical system according to claim 16, wherein the control signal is configured to effect an interruption of the dialysis treatment performed by the hemodialysis apparatus.

18. A method for predicting a rapid blood pressure decrease in a patient undergoing hemodialysis treatment, comprising the steps of:
registering an electrocardiogram signal ($H_{ECG}$) of the patient; and
producing a heart rate variability signal ($p_{HRV}$) based on the electrocardiogram signal ($H_{ECG}$), based on the substeps of:
determining an intensity of ectopic beats ($p_{EBC}$) based on the electrocardiogram signal ($H_{ECG}$);
investigating whether the intensity of ectopic beats ($p_{EBC}$) for a current period is relatively high or relatively low;
during periods of relatively low ectopic beat intensity ($P_{EBC}$):
triggering an alarm signal ($\forall$) indicative of an estimated rapid blood pressure decrease if the heart-rate-variability signal ($p_{HRV}$) fulfills a first alarm criterion, and during periods of relatively high ectopic beat intensity ($p_{EBC}$):
triggering said alarm signal ($\forall$) if the intensity of ectopic beats ($p_{EBC}$) fulfills a second alarm criterion.

19. The method according to claim 18, wherein at least during periods of relatively low ectopic beat intensity ($p_{EBC}$):
transforming an enhanced electrocardiogram signal ($ECG_{CL}$) based on the electrocardiogram signal ($H_{ECG}$) into a power spectrum representation;
calculating a ratio between a low-frequency band and a high-frequency band of said power spectrum to represent the heart-rate-variability signal ($P_{HRV}$); and
regarding the first alarm criterion as fulfilled if the ratio is below a first threshold value.

20. The method according to claim 19, wherein the low-frequency band ranging from approximately 0.04 Hertz to approximately 0.15 Hertz, the high-frequency band ranging from approximately 0.15 Hertz to approximately 0.04 Hertz, and the first threshold value being approximately equal to one.

21. The method according to claim 19 or 20, wherein the second alarm criterion is regarded as fulfilled if the intensity of ectopic beats ($P_{EBC}$) exceeds a second threshold value, said second threshold value representing a number equivalent to approximately four times a mean intensity of the ectopic beats.

22. The method according to claim 21, wherein the mean intensity of ectopic beats is calculated in a sliding window over the enhanced electrocardiogram signal ($ECG_{CL}$).

23. The method according to claim 19, wherein any detected ectopic beat is excluded from the enhanced electrocardiogram signal ($ECG_{CL}$) before calculating said ratio.

24. The method according to claim 23, wherein said excluding of ectopic beats includes excluding each non-ectopic beat following an ectopic beat.

25. The method according to claim 18, further comprising the steps of:
determining at least one heart-rate-turbulence parameter ($P_{HRT}$) based on the electrocardiogram signal ($H_{ECG}$), and during periods of relatively high ectopic beat intensity ($P_{EBC}$);
triggering the alarm signal ($\forall$) if the at least one heart-rate-turbulence parameter ($P_{HRT}$) fulfills at least one third alarm criterion.

26. The method according to claim 25, wherein the at least one heart-rate-turbulence parameter ($P_{HRT}$) comprises at least one of:
a first parameter (TO) expressing a turbulence-onset measure reflecting a relative change in the RR-intervals of the electrocardiogram signal ($H_{ECG}$); and
a second parameter (TS) expressing a turbulence-slope measure reflecting a rise rate of the RR-intervals during a period following a particular ventricular ectopic beat.

27. The method according to claim 26, wherein the at least one third alarm criterion is fulfilled if:
the first parameter (TO) exceeds a first turbulence threshold value; or
the second parameter (TS) is outside an interval delimited by a lower second turbulence value and an upper second turbulence value.

28. The method according to claim 27, further comprising the step of:
determining the first parameter (TO) as a difference between an average RR-interval shortly after ($RR_1$, $RR_2$) a particular ventricular ectopic beat and an average RR-interval shortly before ($RR_{-2}$, $RR_{-1}$) the particular ventricular ectopic beat divided by the average RR-interval shortly before ($RR_{-2}$, $RR_{-1}$) said particular ventricular ectopic beat, said first turbulence threshold value representing a zero alteration of the RR-interval from shortly before to shortly after said ventricular ectopic beat.

29. The method according to claim 27 or 28, further comprising the step of:
determining the second parameter (TS) based on a steepest slope found over a first set of RR-intervals within a second set of RR-intervals following immediately after said ventricular ectopic beat in a function expressing a time difference between consecutive R waves in the electrocardiogram signal ($H_{ECG}$), said lower second turbulence value representing one millisecond per RR-interval.

30. A computer readable medium, having a program recorded thereon, said program being configured to make a computer control the steps of claim 18.

* * * * *

UNITED STATES PATENT AND TRADEMARK OFFICE
CERTIFICATE OF CORRECTION

Page 1 of 1

PATENT NO. : 8,060,190 B2
APPLICATION NO. : 11/662480
DATED : November 15, 2011
INVENTOR(S) : Leif Sörnmo et al.

It is certified that error appears in the above-identified patent and that said Letters Patent is hereby corrected as shown below:

In Claim 7, col. 20, line 4, "claimes 4 5, or 6" should read -- claims 4, 5, or 6 --.

Signed and Sealed this
Fourteenth Day of February, 2012

David J. Kappos
*Director of the United States Patent and Trademark Office*